United States Patent
Li et al.

(10) Patent No.: US 6,660,022 B1
(45) Date of Patent: *Dec. 9, 2003

(54) ROTOR BLADE ANCHOR AND TOOL FOR INSTALLING SAME

(75) Inventors: Lehmann K. Li, Milford, CT (US); Ernie Corrao, Bethel, CT (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,777

(22) Filed: May 26, 2000

Related U.S. Application Data

(60) Provisional application No. 60/136,914, filed on Jun. 1, 1999.

(51) Int. Cl.$^7$ .......................... A61B 17/04; A61B 17/56
(52) U.S. Cl. .......................................... 606/232; 606/60
(58) Field of Search .......................... 606/232, 60, 72; 29/453; 411/80.1; 405/259.1

(56) References Cited

U.S. PATENT DOCUMENTS

| | | |
|---|---|---|
| 2,213,715 A | 9/1940 | Monahan |
| 4,741,330 A | 5/1988 | Hayhurst |
| 4,759,765 A | 7/1988 | Van Kampen |
| 4,776,330 A | 10/1988 | Chapman et al. |
| 4,823,794 A | 4/1989 | Pierce |
| 4,898,156 A | 2/1990 | Gatturna et al. |
| 5,002,574 A | 3/1991 | May et al. |
| 5,041,129 A | 8/1991 | Hayhurst et al. |
| 5,163,946 A | 11/1992 | Li |
| 5,203,787 A | 4/1993 | Noblitt et al. |
| 5,217,486 A | 6/1993 | Rice et al. |
| 5,354,298 A | 10/1994 | Lee et al. |
| 5,372,604 A | 12/1994 | Trott |
| 5,443,482 A | 8/1995 | Stone et al. |
| 5,464,425 A | 11/1995 | Skiba |
| 5,464,427 A | 11/1995 | Curtis et al. |
| 5,486,197 A | 1/1996 | Le et al. |
| 5,531,792 A | 7/1996 | Huene |
| 5,540,718 A | 7/1996 | Bartlett |
| 5,545,180 A | 8/1996 | Le et al. |
| 5,569,303 A | 10/1996 | Johnson |
| 5,662,681 A | 9/1997 | Nash et al. |
| 5,941,882 A | 8/1999 | Jammet et al. |
| 6,068,648 A | 5/2000 | Cole et al. |
| 6,102,934 A | 8/2000 | Li |
| 6,117,161 A | 9/2000 | Li et al. |
| 6,451,030 B2 | 9/2002 | Li et al. |

*Primary Examiner*—Michael J. Milano
*Assistant Examiner*—P Roberts
(74) *Attorney, Agent, or Firm*—Smith & Nephew, Inc.; George K. Stacey

(57) ABSTRACT

An insertion tool for a rotor blade anchor. The anchor is pivotably coupled to a handle so that the anchor can assume a first position in alignment with the longitudinal axis of the handle. The tool is designed to be rotated about the longitudinal axis so that the anchor, when placed in a bore hole in biological tissue, can attain a second position substantially perpendicular to the longitudinal axis. The anchor itself includes a cutting surface thereon. A deploy spring is disposed on the handle and biases the anchor toward the second position. In use, when the rotor blade is inserted into an object such as a bone, the object moves the anchor toward alignment with the longitudinal axis. When the anchor is inserted far enough into the object, a user rotates the handle and the anchor. The deploy spring biases the cutting surface so that is engages with the sidewall of the borehole. The rotation of the handle causes the cutting surface to cut into the object. The rotation imparted by the user and the biasing produced by the deploy spring causes the anchor to undergo a screwing type motion as it is being inserted into the object. Eventually the anchor attains a position substantially perpendicular to the longitudinal axis.

9 Claims, 3 Drawing Sheets

ROTOR BLADE ANCHOR AND TOOL FOR INSTALLING SAME

CROSS-REFERENCE RELATED APPLICATIONS

This application claims priority to provisional application No. 60/136,914 filed Jun. 1, 1999.

BACKGROUND OF THE INVENTION

The invention relates to fasteners or anchors and, more particularly, to fasteners or anchors for securement into biological tissue, particularly bone. The invention finds particular application in the securement of sutures to bone, such as the attachment of torn ligaments or ligament replacements to the bone through attachment of the suture to the anchor.

In the medical field, it is frequently necessary to securely attach elements such as ligaments (e.g. rotator cuff ligaments, anterior cruciate ligaments) and prosthetics, to a bone. Such attachment requires, initially, that an anchor be secured within the bone itself. Once the anchor is secured, the ligament or prosthetic can be attached to the anchor through, for example, sutures extending from the anchor.

Various techniques exist for securing an anchor within a bone. In co-pending U.S. application Ser. No. 08/470,988 now U.S. Pat. No. 5,792,165 assigned Li Medical Technologies, Inc., for example, a longitudinally extending groove is first drilled within the bone. An anchor disposed perpendicularly to an insertion handle, is then inserted into the groove and screwed into the bone until the anchor is held securely therein. Since the anchor is disposed perpendicularly to the handle, it is necessary to prepare a groove large enough to accommodate the size of the anchor including its entire length.

Bones are made of a relatively hard outer layer of tissue made of cortical bone cells and a softer inner layer of tissue made of cancellous cells. By making such grooves in the bone, a larger amount of the harder cortical bone cells must be removed thereby decreasing the affixment strength available for securing the anchor within the bone.

In co-pending U.S. application Ser. No. 09/088,572 now U.S. Pat. No. 6,102,934 also assigned to Li Medical Technologies, Inc., a rotor blade inserter includes a pushing member having a cam surface thereon that engages with an anchor. The pushing member slides in a channel. A collar is disposed on and threaded with the handle. When the collar is rotated, the collar traverses along the handle, transferring the translational motion to the pushing member, which in turn produces a rotational movement of the anchor through the engagement of the anchor with the cam surface. In order to insert the anchor into a bone, a user must rotate a handle of the device and also manipulate the collar. This operation can be quite cumbersome and difficult to effectuate. An embodiment is disclosed where a spring trigger can be used to apply a force upon the pushing channel when the spring trigger is actuated. However, actuation of the trigger is an additional manipulation which must be performed. In many surgical applications, a surgeon's hands are occupied by numerous tasks and so it is important to provide a device which can be actuated with as few movements as possible and/or with one hand.

In U.S. Pat. No. 5,203,787 to Noblitt et al., a hole is drilled in a bone and then an anchoring device is inserted into the hole so that a longitudinal axis of the anchoring device is parallel to a longitudinal axis of the hole. A force is then applied to a suture coupled to the anchoring device thereby causing the anchoring device to rotate within the cancellous cells of the bone so that the anchor extends perpendicularly to the longitudinal axis of the hole. The anchor is then held within the bone by abutting against the inside of the harder cortical bone cells. The technique of Noblitt et al., however, requires complex manipulation of the suture to achieve the desired orientation of the anchor.

Moreover, modem trends in surgery include the restoration of bodily function and form, or repair of anatomical structures through the use of minimally invasive surgical techniques. The ability to surgically repair damaged tissues or joints creating as few and as small incisions as possible, and with ease of manipulation, produces less trauma to the patient, less pain and generally better clinical outcomes.

Thus, there exists a need in the art for a minimally invasive method and device which more securely attaches an anchor within a bone than devices and techniques of the prior art.

SUMMARY OF THE INVENTION

One aspect of the invention is a method for securing an anchor to biological tissue, the anchor being detachably and pivotably mounted to an insertion tool, the anchor having a longitudinal axis, the insertion tool having a first axis that extends longitudinally with respect to the insertion tool, and a second axis which extends perpendicularly to the first axis. The method comprises the steps of holding the anchor with the insertion tool; and applying a biasing force to the anchor to bias the anchor toward a position that is substantially perpendicular to the first axis. The method further comprises the steps of inserting the anchor held by the insertion tool, with the longitudinal axis of the anchor being disposed in an orientation that is not perpendicular to the first axis, into a borehole in the biological tissue; and rotating the anchor about the first axis, the biasing force causing the anchor to engage with a sidewall of the bore hole and to penetrate into the sidewall. In this way, the anchor is screwed into the object as the insertion tool is rotated about the first axis until the anchor achieves an orientation substantially perpendicular to the first axis.

Another aspect of the invention is a tool for securing an anchor to biological tissue. The tool comprises a handle, the handle having a first axis that extends longitudinally with respect to the handle, and a second axis that extends perpendicularly to the first axis; an anchor pivotably coupled to the handle so that the anchor is pivotable about the second axis; and a biasing member disposed in or on the handle, the biasing member biasing the anchor toward a position which is substantially perpendicular to the first axis. The handle being rotatable about the first axis to allow the anchor to rotate about the first axis, the biasing member causing the anchor to penetrate into a bore hole in the biological tissue by pivoting about the second axis, and to screw into the bore hole to attain a position which is substantially perpendicular to the first axis when the anchor is inserted into the bore hole in the biological tissue.

Yet another aspect of the invention is a tool for securing an anchor to biological tissue. The tool comprising a handle, the handle having a first axis that extends longitudinally with respect to the handle, and a second axis that extends perpendicularly to the first axis; an anchor pivotably coupled to the handle so that the anchor is pivotable about the second axis; and a biasing member disposed on the handle, the biasing member biasing the anchor toward a position which is substantially perpendicular to the first axis.

These aspects, as well as others, will become apparent upon reading the following disclosure and corresponding drawings.

BRIEF DESCRIPTION OF THE DRAWINGS

For the purpose of illustrating the invention, there is shown in the drawings a form which is presently preferred, it being understood, however, that the invention is not limited to the precise arrangements and instrumentalities shown.

DETAILED DESCRIPTION OF THE INVENTION

Figure 1:
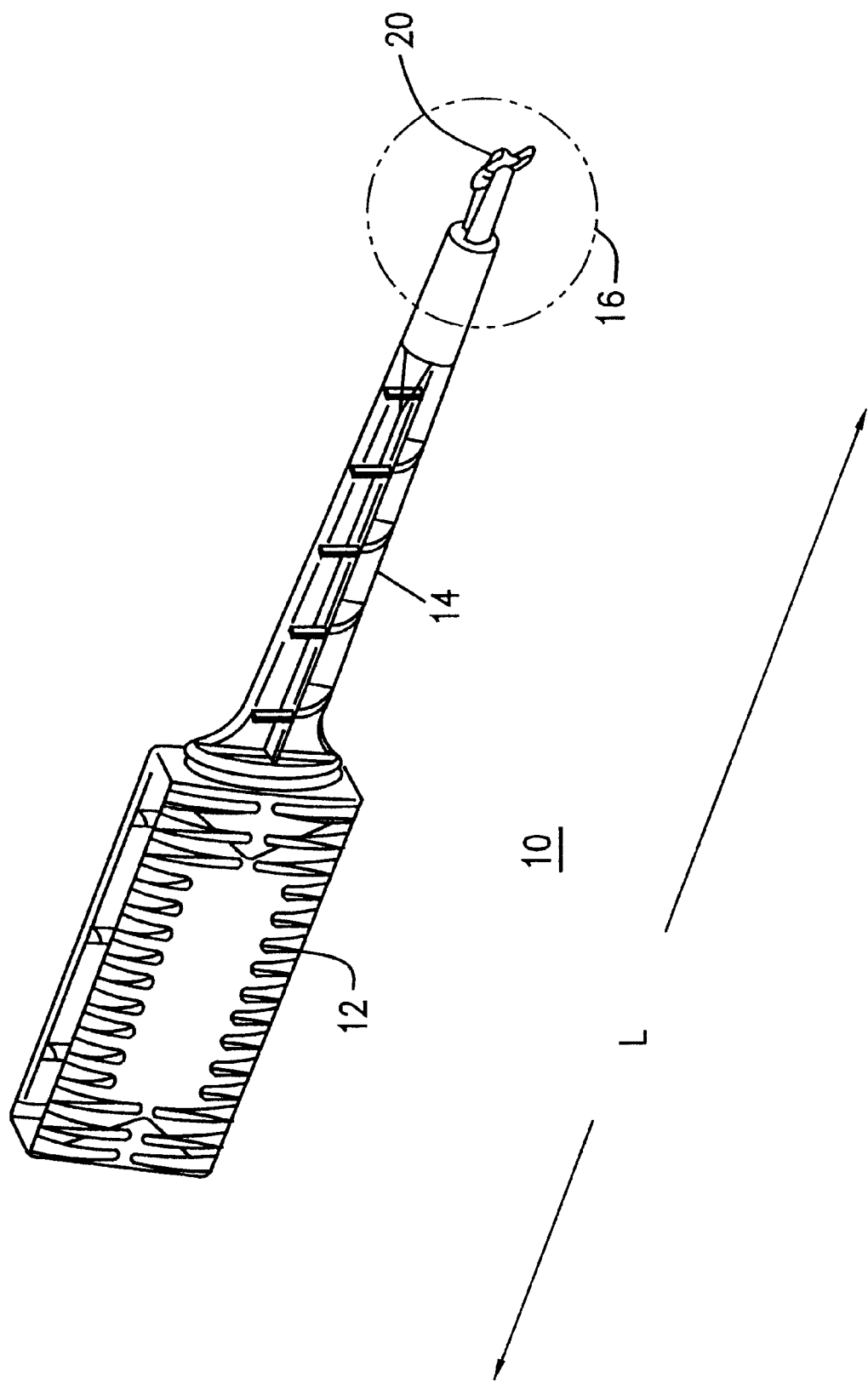
FIG. 1 is perspective view of a rotor blade anchor and tool in accordance with the invention.

Referring to FIG. 1, there is shown generally a tool 10 for installing a rotor blade anchor in accordance with the invention. Tool 10 includes a handle 12 at one end, a distal tip 16 holding a rotor blade anchor 20 at the distal end, and a shaft portion 14 connecting handle 12 to distal tip 16.

Figure 2:
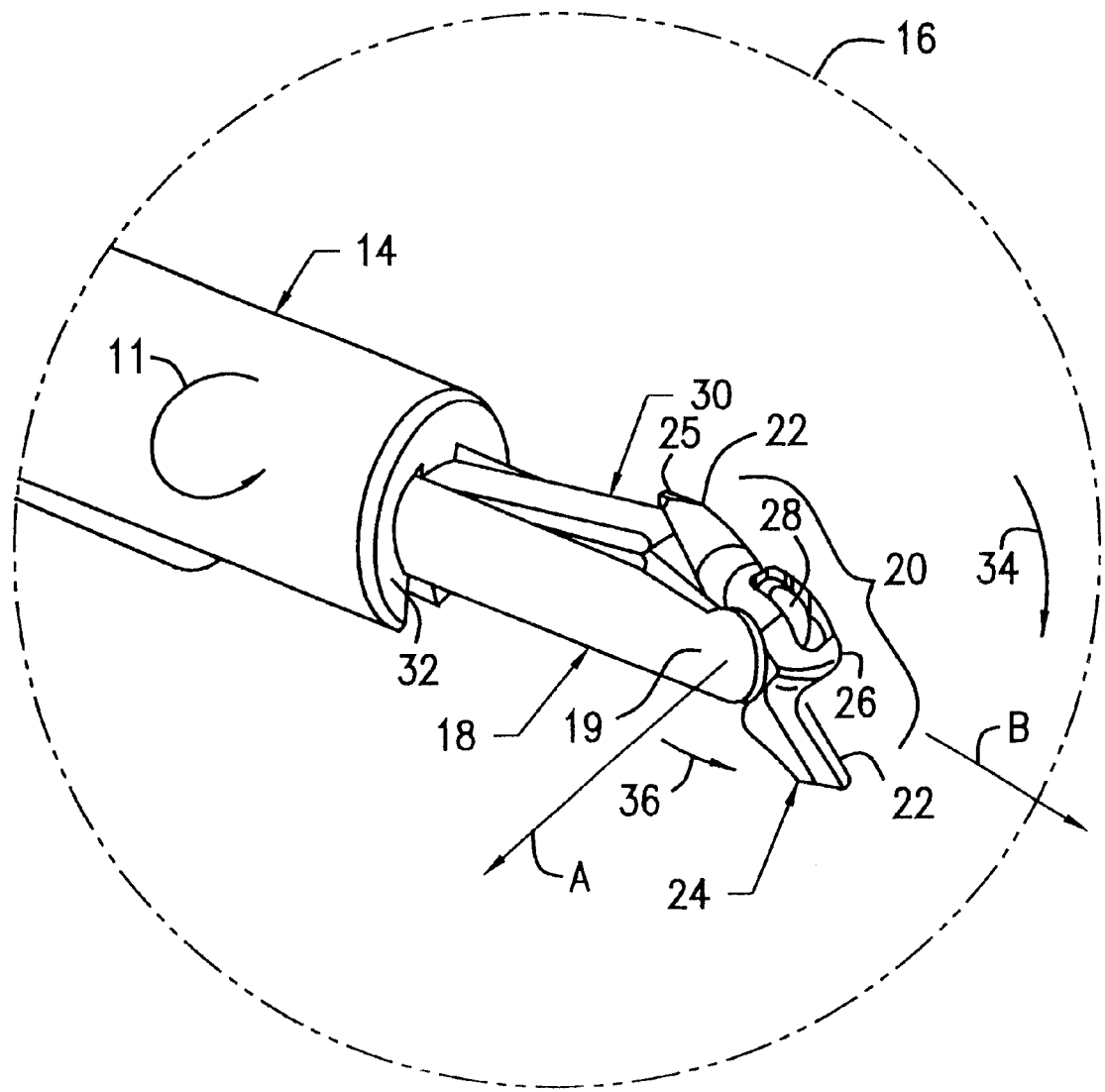
FIG. 2 is an enlarged perspective view of a rotor tip of the rotor blade anchor and tool of FIG. 1.
Figure 3:
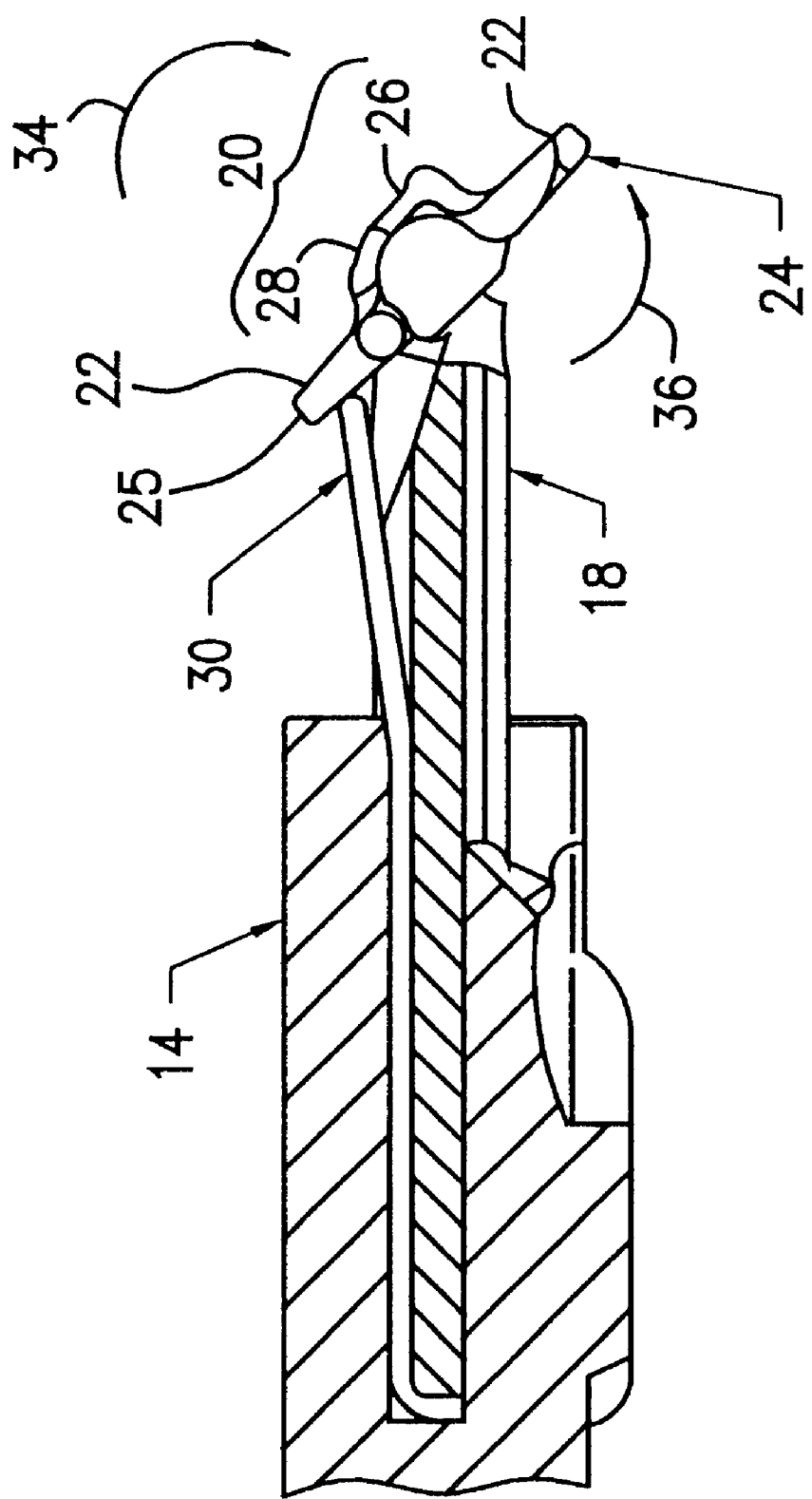
FIG. 3 is a side view of the rotor tip of FIG. 2.

Referring also to FIGS. 2 and 3, distal tip 16 includes a rotor tip 18 adapted to hold rotor blade anchor 20. Anchor 20 has a sharp leading edge cutting portion 22 on at least one of a leading side 24 and a trailing side 25 of anchor 20. Anchor 20 further includes a hub 26 disposed at a generally central portion thereof, having an opening 28 allowing sutures (not shown) to be threaded therethrough. Hub 26 can include other attachment devices such as a screwhole, threaded shaft, rod, etc. Anchor 20 may be, for example, oval, kidney, pointed, circular disc, or polygonal shaped. Anchor 20 may be symmetrical or asymmetrical and may be solid or with fenestrations. It should be clear that other shapes are possible for anchor 20. Anchor 20 could be made of, for example, metal, a polymer, a bioabsorbable material, another biocompatible material, a bone material, e.g. an allograft or autograft, or any other appropriate material.

Rotor tip 18 can be coupled to anchor 20 through any appropriate means. For example, rotor tip 18 can have spanner type protrusions (not shown) that mate with slots (not shown) on anchor 20. When anchor 20 is fully inserted into a bone, the spanner type protrusions can be easily removed from the slots thereby leaving the anchor secured within the bone. As an alternative, though it should be clear that these are not the only possible ways of coupling rotor tip 18 with anchor 20, rotor tip 18 may have cylindrical protrusions (not shown) extending inwardly. These cylindrical protrusions engage with corresponding voids (not shown) in anchor 20. In this way, anchor 20 would be easily pivotably coupled to and removable from rotor tip 18.

Rotor tip 18 further includes a deploy spring 30 disposed therein. Deploy spring 30 acts as a biasing member and biases anchor 20 toward a position that is generally perpendicular to a longitudinal axis L (see FIG. 1) of the axis of shaft 14 of tool 10—though anchor 20 is shown extending in a position that is generally oblique to longitudinal axis L. In the figures, this biasing force causes anchor 20 to rotate generally clockwise in direction 34. Deploy spring 30 may be, for example, a leaf spring as shown, or any other suitable element for providing a biasing force that tends to rotate anchor 20.

The invention allows a user to implant an anchor into a bore in body tissue, e.g., a bone, while minimizing the amount of bone tissue that is necessary to be removed to allow entry of the anchor. When anchor 20 is to be inserted into bone, a hole is drilled in the bone to make a bone hole that is large enough to accommodate a perimeter defined by a cross-section of rotor tip 18. Unlike some prior art devices, it is not necessary to drill a hole in the bone that has a surface cross-sectional length to accommodate the length of the anchor. This is because anchor 20 is pivoted with respect to rotor tip 18 so that only leading side 24 of anchor 20 is initially inserted into the hole in the bone (as is discussed more completely below).

When anchor 20 held by shaft 14 is inserted into the bone hole, the inner periphery of the bone hole causes anchor 20 to pivot against the biasing force of deploy spring 30 (in the drawings, this would result in a counter-clockwise movement shown at 36) thereby compressing deploy spring 30 and minimizing the periphery of distal tip 16 that is inserted into the bone hole. When anchor 20 has been inserted into the bone hole a certain distance as limited by a shoulder 32 contacting the bone surface, the user of tool 10 rotates handle 12 in a direction so as to allow cutting edge 22 to begin to cut into the bore hole initially due to the biasing force applied by spring 30. In the illustrated embodiment, this rotation is in the direction of arrow 11. Such rotation will impart rotation to anchor 20 and cause anchor 20 to cut into the bone due to the presence of cutting edges 22 on anchor 20. As anchor 20 is cutting into the bone, cutting edge 22 of leading side 24 and trailing side 25 pivot anchor 20 outwardly in direction 34 so that anchor 20 traverses in a helical or corkscrew motion to a position which is substantially perpendicular to longitudinal axis L of rotor blade 10. Simultaneously, anchor 20 is being rotated about longitudinal axis L. As a consequence, anchor 20 undergoes a corkscrew or helical movement within the bore hole as anchor 20 is being rotated with respect to two axes. Anchor 20 accordingly is pivoted about a first axis (axis A) initially by the biasing force of spring 30 and thereafter by the geometry of the cutting edge 22, and rotated about a second axis (axis B) by rotational movement imparted by the user turning handle 12. While anchor 20 is being inserted into the bone, the user is also provided with tactile feedback relating to the anchor engagement within the bone hole—similar to emplacing a screw anchor into a bone.

Optional shoulder 32 can be disposed on rotor tip 18 extending outwardly therefrom. When rotor blade 10 has been inserted into the bone hole to a desired depth, shoulder 32 will abut against the outer surface of the cortical bone cells thereby inhibiting further insertion of rotor blade 10. Shoulder 32 thereby allows for more precise and reliable engagement of anchor 20 within the bone tissue.

When anchor 20 is secured within the bone hole and extends substantially perpendicular to longitudinal axis L, handle 12 and insertion portion 14 are detached from anchor 20. This can be performed by a suitable mechanism (not shown) such as a mechanism for spreading two opposed elements 19 of rotor tip 18 so that they disengage from anchor 20. Sutures (not shown) can be unwound from handle 12 as handle 12 is detached from anchor 20 so that the sutures extend outwardly from the bone hole.

Tool 10 can be designed for a single use (i.e. disposable) or so as to be reusable. It can be designed for open or minimally invasive surgery.

Thus, by providing an anchor which can rotate to extend parallel and perpendicular to an insertion member, a smaller insertion opening can be made in a bone than with anchor securement techniques of the prior art. This minimizes the trauma caused to the biological tissues and enhances the attachment of the anchor to the bone because less of the bone cells are removed. The tool and anchor are also simpler and more convenient than many prior art techniques.

While preferred embodiments of the invention have been disclosed, various modes of carrying out the principles disclosed herein are contemplated as being within the scope of the following claims. Therefore, it is understood that the scope of the invention is not to be limited except as otherwise set forth in the claims.

What is claimed is:

1. A method for securing an anchor to biological tissue, said anchor being detachably and pivotably mounted to an insertion tool, said anchor having a longitudinal axis, said insertion tool having a first axis that extends longitudinally with respect to said insertion tool, and a second axis which extends perpendicularly to said first axis, said method comprising the steps of:

holding said anchor with said insertion tool;

applying a biasing force to said anchor to bias said anchor and cause said anchor to rotate about said second axis toward a position that is substantially perpendicular to said first axis, said step of applying a biasing force and causing said anchor to rotate about said second axis being accomplished through the use of a biasing member of said insertion tool, said biasing member moving radially outwardly to cause said anchor to rotate about said second axis;

inserting said anchor held by said insertion tool, with said longitudinal axis of said anchor being disposed in an orientation that is not perpendicular to said first axis, into a borehole in said biological tissue; and rotating said anchor about said first axis, said biasing force causing said anchor to engage with a sidewall of said bore hole and to penetrate into said sidewall;

whereby said anchor is screwed into said biological tissue as said insertion tool is rotated about said first axis until said anchor achieves an orientation substantially perpendicular to said first axis.

2. The method as claimed in claim 1, wherein in said inserting step, said longitudinal axis of said anchor is substantially parallel to said first axis.

3. The method as claimed in claim 1, wherein in said inserting step, said longitudinal axis of said anchor is oblique to said second axis.

4. The method as claimed in claim 1, wherein said biological tissue has an outer layer and an inner layer, said outer layer having a strength that is greater than a strength of said inner layer, and wherein said step of inserting includes inserting said anchor into said inner layer.

5. The method as claimed in claim 1, wherein said biological tissue is a bone.

6. The method as claimed in claim 4, wherein:

said biological tissue is bone;

said outer layer is cortical tissue of said bone; and said inner layer is cancellous tissue of said bone.

7. The method as claimed in claim 1, further comprising detaching said insertion tool from said anchor.

8. The method as claimed in claim 1, wherein said anchor includes at least one cutting edge disposed thereon to penetrate into said sidewall.

9. A method for securing an anchor to biological tissue, said anchor being detachably and pivotably mounted to an insertion tool, said anchor having a longitudinal axis, said insertion tool having a first axis that extends longitudinally with respect to said insertion tool, and a second axis which extends perpendicularly to said first axis, said method comprising the steps of:

holding said anchor with said insertion tool;

applying a biasing force to said anchor to bias said anchor and cause said anchor to rotate about said second axis toward a position that is substantially perpendicular to said first axis;

inserting said anchor held by said insertion tool, with said longitudinal axis of said anchor being disposed in an orientation that is not perpendicular to said first axis, into a borehole in said biological tissue; and rotating said anchor about said first axis, said biasing force causing said anchor to engage with a sidewall of said bore hole and to penetrate into said sidewall;

whereby said anchor is screwed into said biological tissue as said insertion tool is rotated about said first axis until said anchor achieves an orientation substantially perpendicular to said first axis;

wherein said step of applying a biasing force to bias said anchor and cause said anchor to rotate about said second axis is accomplished through the use of a biasing member of said insertion tool and further wherein said step of inserting further includes compressing said biasing member so that an outer periphery of the combination of said anchor and said biasing member is smaller than an outer periphery of said combination when said anchor does not compress said biasing member.

* * * * *